Figure 1:
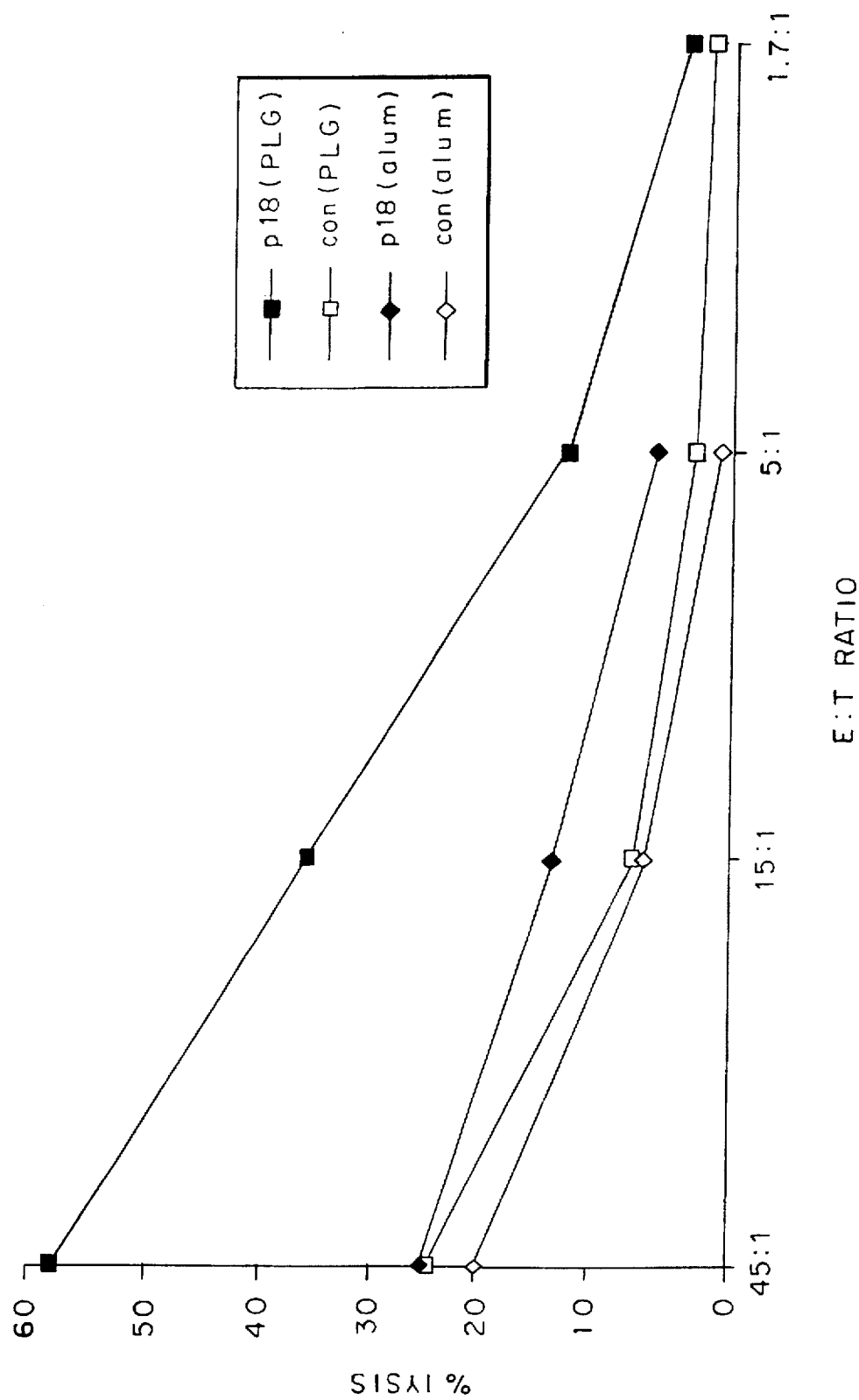

United States Patent [19]
Burnett et al.

[11] Patent Number: 5,762,965
[45] Date of Patent: Jun. 9, 1998

[54] VACCINES AGAINST INTRACELLULAR PATHOGENS USING ANTIGENS ENCAPSULATED WITHIN BIODEGRADBLE-BIOCOMPATIBLE MICROSPHERES

[75] Inventors: Paul R. Burnett, Silver Spring; John E. Van Hamont, Ft. Meade; Robert H. Reid, Kensington, all of Md.; Jean A. Setterstrom, Alpharetta, Ga.; Thomas C. Van Cott, Brookeville; Debrah L. Birx, Potomac, both of Md.

[73] Assignee: The United States of America as represented by the Secretary of the Army, Washington, D.C.

[21] Appl. No.: 598,874

[22] Filed: Feb. 9, 1996

Related U.S. Application Data

[63] Continuation-in-part of Ser. No. 242,960, May 16, 1994, and Ser. No. 446,149, May 22, 1995, which is a continuation of Ser. No. 590,308, Mar. 16, 1984, abandoned, said Ser. No. 242,960, is a continuation-in-part of Ser. No. 867,301, Apr. 10, 1992, Pat. No. 5,417,986, which is a continuation-in-part of Ser. No. 805,721, Nov. 21, 1991, abandoned, which is a continuation-in-part of Ser. No. 690,485, Apr. 24, 1991, abandoned, which is a continuation-in-part of Ser. No. 521,945, May 11, 1990, abandoned.

[51] Int. Cl.$^6$ .............................. A61K 9/00; A61K 9/66; A61K 9/14; A61F 13/00
[52] U.S. Cl. .................... 424/499; 424/426; 424/455; 424/486; 424/488; 424/422
[58] Field of Search .................... 424/499, 426, 424/455, 486, 488, 422

[56] References Cited

U.S. PATENT DOCUMENTS

| 4,863,735 | 9/1989 | Kohn et al. ............... 424/422 |
| 4,897,268 | 1/1990 | Tice et al. ................ 424/422 |

Primary Examiner—Theodore J. Criares
Attorney, Agent, or Firm—Werten F. W. Bellamy

[57] ABSTRACT

This invention relates to parenteral and mucosal vaccines against diseases caused by intracellular pathogens using antigens encapsulated within a biodegradable-biocompatible microspheres(matrix).

14 Claims, 2 Drawing Sheets

VACCINES AGAINST INTRACELLULAR PATHOGENS USING ANTIGENS ENCAPSULATED WITHIN BIODEGRADBLE-BIOCOMPATIBLE MICROSPHERES

II. CROSS REFERENCE

This application is a continuation-in-part of U.S. patent application Ser. No. 08/242,960, filed May 16, 1994, pending; which in turn is a continuation-in-part of U.S. patent application Ser. No. 07/867,301 filed Apr. 10, 1992, now U.S. Pat. No. 5,417,986 which in turn is a continuation-in-part of U.S. patent application Ser. No. 07/805,721 filed Nov. 21, 1991; now abandoned, which in turn is a continuation-in-part of U.S. patent application Ser. No. 07/690,485 filed Apr. 24, 1991, now abandoned; which in turn is a continuation-in-part of U.S. patent application Ser. No. 07/521,945 filed May 11, 1990, now abandoned. Additionally, this application is a continuation-in-part of U.S. patent application Ser. No. 08/446,149 filed May 22, 1995, pending; which in turn is a continuation of U.S. patent application Ser. No. 06/590,308 filed Mar. 16, 1984, now abandoned.

I. GOVERNMENT INTEREST

The invention described herein may be manufactured, licensed and used by or for governmental purposes without the payment of any royalties to us thereon.

III. FIELD OF THE INVENTION

This invention relates to parenteral and mucosal vaccines against diseases caused by intracellular pathogens using antigens encapsulated within biodegradable-biocompatible microspheres(matrix).

IV. BACKGROUND OF THE INVENTION

Most infections by viruses and other intracellular pathogens are countered in the human host by a combination of humoral (antibody) and cellular (lymphocyte and phagocyte) immune effectors. Although the precise identity of immune effectors capable of protecting the host against some chronic intracellular pathogens (e.g. HIV-1) remains unknown, attempts to develop preventive and therapeutic vaccines still focus on the induction of appropriate humoral and cellular immune responses. Furthermore, since most human viral pathogens (including HIV-1) are transmitted across mucosal surfaces, it is important that vaccines induce such responses locally (at the mucosal surface) as well as systemically and that they be durable for long-term protection.

The issues of durability and mucosal immunogenicity have been previously addressed by encapsulating vaccine antigens in appropriately-sized biodegradable, biocompatible microspheres made of lactide/glycolide copolymer (the same materials used in resorbable sutures). It has been shown that such microspheres can be made to release their load in a controlled manner over a prolonged period of time and can facilitate the interaction of their contents with the local immune system when administered mucosally.

In the case of HIV-1 infection, there is insufficient information at this time regarding the virus and its interactions with the human immune system to permit the rational design of a preventive vaccine. However, it has been noted that many candidate HIV vaccines tested to date fail to elicit antibodies capable of neutralizing wild-type HIV-1 or binding to native HIV-1 proteins, fail to induce a substantial population of effector cells capable of destroying HIV-1-infected cells, and fail to induce significant responses at mucosal surfaces. A possible approach to overcoming these problems (applicable to both HIV-1 and other chronic intracellular pathogens) is to identify a native protein, accessible to the immune system on the surface of both free virus and infected cells, and present it to the immune system (systemic and mucosal) encapsulated in microspheres to protect and augment its immunogenicity.

V. DESCRIPTION OF DRAWINGS

FIG. 1 indicates control induction in mice immunized with rgp 160; and

Figure 2:
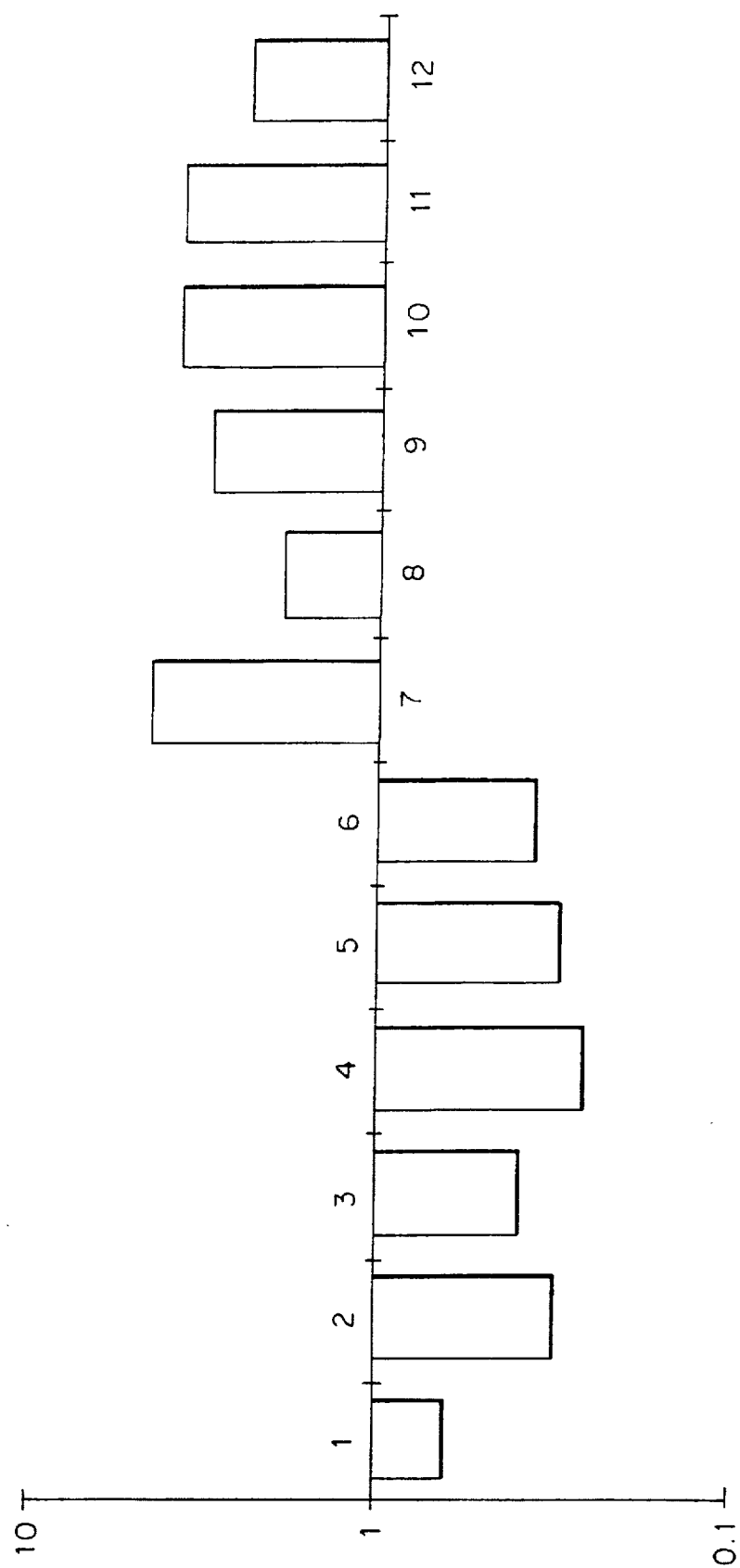

FIG. 2 indicates "Native"/denatured rgp 120 (IIIB) Binding Ratios.

V. DESCRIPTION OF THE INVENTION

This invention relates to a novel pharmaceutical composition, a microcapsule/sphere formulation, which comprises an antigen encapsulated within a biodegradable polymeric matrix, such as poly(DL-lactide co glycolide) (PLG), wherein the relative ratio between the lactide and glycolide component of the PLG is within the range of 52:48 to 0:100, and its use, as a vaccine, in the effective induction of antiviral immune responses comprising both virus-specific cytotoxic T lymphocytes and antibodies reactive against native viral antigens. In the practice of this invention, applicants found that when a complex (oligomeric) native envelope protein of HIV-1 was encapsulated in PLG microspheres, it retained its native antigenicity and function upon its release in vitro. Furthermore, when used as a vaccine in animals, this product elicited HIV-specific cytotoxic T lymphocytes and antibodies reactive with native (oligomeric) HIV-1 envelope protein.

The following examples illustrate the invention:

EXAMPLE 1

Materials and Methods

Immunogens. Non-CD4-binding, baculo-expressed, recombinant gp $160_{IIIB}$ (rgp 160) was obtained from MicroGeneSys (Meriden, Conn.). CD4-binding, oligomeric gp 160 CDC451 (o-gp 160) was obtained from Advanced BioScience Laboratories (Kensington, Md.).

Microencapsulation of immunogens: PLG microspheres ranging from 1 to 20 um in diameter and containing a 0.5 to 1.0% antigen core load were prepared by a solvent extractive method. The solvent extraction method involves dissolving the viral antigen and sucrose (1:4 ratio w:w) in 1 ml of deionized water. This solution is flash frozen and lyophilized. The resulting antigen-loaded sucrose particles are resuspended in acetonitrile and mixed into PLG copolymer dissolved in acetonitrile. This antigen-polymer mixture is then emulsified into heavy mineral oil, transferred into heptane and mixed for 30 min to extract the oil and acetonitrile from the nascent spheres. The spheres are harvested by centrifugation, washed three times in heptane and dried overnight under vacuum. Microsphere size was determined by both light and scanning electron microscopy. The antigen core load was determined by quantitative amino acid analysis of the microspheres following complete hydrolysis in 6N hydrochloric acid.

Analysis of immunogen spontaneously released from microspheres in vitro by binding to soluble CD4 and recognition by HIV-positive patient serum. PLG microspheres loaded with native (oligomeric) gp 160 were suspended in phosphate-buffered saline, pH 7.4 (PBS), incubated at 37 C. for 3 h, and then at 4 C overnight. The microspheres were then sedimented by centrifugation (2 min at 200×g), the supernatants harvested, and the released gp 160 assayed for binding to CD4 and recognition by HIV-positive patient serum by surface plasmon resonance (described below). A sample of the stock protein used for microencapsulation was assayed for comparison.

Immunization of animals. HIV-seronegative, 8-10 week old NZW rabbits were immunized intramuscularly with rgp 160- or o-gp 160-loaded PLG microspheres suspended in PBS or with alum-adjuvanted rgp 160 in PBS. Groups receiving rgp 160-loaded microspheres (n=2) were primed with 50 ug of immunogen on day 0 and boosted with 25 ug on day 42. Groups receiving o-gp 160-loaded microspheres (n=3) were primed with 70 ug of immunogen on day 0 and boosted with 35 ug on day 56. Groups receiving alum-adjuvanted rgp 160 (n=2) got 85 ug of immunogen on days 0, 7, and 28.

BALB/c mice were immunized subcutaneously with rgp 160-loaded PLG microspheres suspended in PBS or with alum-adjuvanted rgp 160 in PBS. The mice in all groups (n=4) received 10 ug of immunogen on days 0 and 21.

Determination of the ratio of antibody binding to "native"/denatured rgp $120_{IIIB}$ measured by surface plasmon resonance (SPR). Real-time binding interactions between ligand (gp 120 covalently linked to a biosensor matrix) and ligate (Abs in solution) were measured using surface plasmon resonance (BIAcore, Pharmacia Biosensor, Piscataway, N.J.). "Native"rgp 120(IIIB) (Genentech, South San Francisco, Calif.) or reduced, carboxymethylated (denatured) rgp 120(IIIB) (Genentech) was covalently linked to the biosensor dextran matrix. Sera and mAbs were diluted in HBS running buffer (10 mM HEPES, 150 mM NaCl, 3.4 mM EDTA, 0.05% (BIAcore) surfactant P20, pH 7.4) and injected through the dextran matrices at a flow rate of 5 ul/min. The binding value of each serum or mAb was measured in resonance units (RU), and the "native"/denatured gp 120 ratios were determined by dividing the corresponding RU values and correcting for small differences in matrix concentration. Controls included an HIV-positive patient serum and mAb 1c1.

Assessment of HIV-specific cell-mediated immunity in immunized mice by secondary CTL assay. The spleens of BALB/c mice immunized on days 0 and 21 were harvested and single cell suspensions prepared aseptically in complete RPMI medium on day 35. The cells were then pooled within experimental groups (n=4), underlay with ficoll, centrifuged 30 min at 450×g (RT), washed, and resuspended in complete RPMI medium. Following a 1 h stimulation with peptide p18 (1 uM) at 37° C., the cell suspensions were diluted with complete RPMI supplemented with 2ME (1:1000) and transferred to flasks for a 6 day incubation at 37° C. After 2 days, recombinant IL-2 (10 u/ml) was added to all flasks. On day 6, P815 target cells were pulsed with peptide p18 (1 uM) or with nothing (control) in PBS supplemented with 0.1% BSA. $3 \times 10^{\wedge}6$ target cells were labelled with 300 uCi of $^{51}$Cr, washed, and plated out with the effector cells at effector-:target (E:T) ratios of 45:1, 15:1, 5:1, and 1.7:1. After a 6 h incubation at 37° C., the supernatants were harvested and counted, and % specific lysis was calculated.

Results

Comparison of the native (oligomeric) gp 160 prior to microencapsulation and following spontaneous release from PLG microspheres showed the two to be essentially indistinguishable in terms of their binding to CD4 and recognition by HIV-positive patient serum. (Table 1). This retention of conformation-dependent binding shows that structure of the antigen is not appreciably altered by the microencapsulation process.

FIG. 1 shows the data from a cytotoxic T lymphocyte (CTL) assay performed on the speen cells of mice which had had been previously immunized with either HIV-1 envelope protein encapsulated in PLG microspheres (dark squares) or the same protein administered in a conventional way with alum adjuvant (dark diamonds). These data indicate that microencapsulation of HIV-1 envelope protein in PLG microspheres results in a vaccine that induces significantly greater anti-HIV CTL activity than does alum-adjuvanted vaccine. The open symbol groups represent controls run to assure that the activity being measured is virus-specific.

FIG. 2 shows the results of an assay designed to measure the relative binding of antibodies to native vs denatured viral protein. These data show that rabbits immunized with a non-native HIV-1 protein encapsulated in PLG (#5 and 6) develop antibodies which show greater binding to denatured (vs native) protein (indicated by a ratio<1). On the other hand, rabbits immunized with a native HIV-1 protein encapsulated in PLG microspheres (#10–12) develop antibodies which show greater binding to native viral protein (indicated by ratio>1). This retention of each proteins antigenicity constitutes an additional piece of evidence that the structure of antigens loaded in PLG microspheres are preserved.

EXAMPLE 2

Materials and Methods

This experiment was similar to that described in Example 1 except for the method of microencapsulation employed.

Microencapsulation of immunogens: PLG microspheres ranging from 1 to 15 um in diameter and containing a 0.5 to 1.0% antigen core load were prepared by a solvent evaporation method. The solvent evaporation method involves emulsifying the viral antigen dissolved in deionized water into poly(DL-lactide-co-glycolide) polymer dissolved in methylene chloride. This emulsion is mixed into 0.9% polyvinyl alcohol and stirred. After 10 min of stirring, 0.35 l of water is added and gentle mixing is continued for 1.5 h. The resulting spheres are harvested by centrifugation, washed three times in distilled water, and dried overnight under vacuum. Microsphere size was determined by both light and scanning electron microscopy. The antigen core load was determined by quantitative amino acid analysis of the microspheres following complete hydrolysis in 6N hydrochloric acid.

Results

Analysis of spontaneously released antigen showed it to retain its CD4 binding capacity. Its native antigenicity (recognition by the serum of an HIV-positive patient) was only slightly less than that of the antigen prior to encapsulation and following spontaneous release from microspheres produced by a solvent extraction method (Table 1).

The results of immunizing animals with either non-native (denatured) or native oligomeric gp 160 in PLG microspheres produced by a solvent evaporation method were essentially indistinguishable from those obtained using microspheres produced by a solvent extraction method (example 1). Microencapsulated antigen induced significantly greater CTL activity than antigen administered in a conventional alum-adjuvanted formulation. Furthermore, preservation of the structure of PLG-microencapsulated antigens is supported by the findings of preferential binding of antibodies elicited by microspheres loaded with denatured antigen to denatured gp 120 (FIGS. 2, 3 and 4) and the preferred binding of antibodies elicited by microspheres loaded with native (oligomeric) antigen to native gp 120 (FIGS. 2, 7–8).

TABLE 1

BIA (released o-gp160)
Capture o-gp160-451 (stock vs microsphere-released)
on tvc 391 fc3/fc4 sCD4 (4 mg/m)
1 ul/min flow rate for o-gp160 inj.; 5 ul/min for all others

| ligate | RU | HIV+/sCD4 (RU ratio) |
|---|---|---|
| gp120-MN 1:10 | 3286 | |
| HIV+ 1:100 | 54 | |
| NHS 1:100 | 3 | |
| HIV+ pool 1:100 | 47 | |
| o-gp160 (tvc281) | 1772 | |
| HIV+ | 3259 | 1.84 |
| tvc281 | 1848 | |
| NHS | −36 | |
| tvc281 | 1762 | |
| HIV+ pool | 2597 | 1.47 |
| tvc281-PLG-EV | 3342 | |
| HIV+ | 4594 | 1.37 |
| tvc281 | 3222 | |
| NHS | 7 | |
| tvc281 | 3210 | |
| HIV+ pool | 3336 | 1.04 |
| tvc281-PLG-EX | 1855 | |
| HIV+ | 3760 | 2.04 |
| tvc281 | 1839 | |
| NHS | 2 | |
| tvc281 | 1850 | |
| HIV+ pool | 2745 | 1.48 |
| gp120-MN 1:10 | 2914 | |
| HIV+ 1:100 | 14 | |
| NHS 1:100 | −2 | |
| HIV+ pool 1:100 | 14 | |
| tvc281 | 1099 | |
| HIV+ | 1083 | 0.99 |
| tvc281 | 1022 | |
| HIV+ pool | 1395 | 1.36 |
| tvc281-PLG-EV | 1595 | |
| HIV+ | 1322 | 0.83 |
| tvc281 | 1535 | |
| HIV+ pool | 1781 | 1.16 |

In view of the above it will be seen that the objects of the invention are achieved. As various changes could be made in the above materials and methods without departing from the scope of the invention, it is intended that all matter contained in the above description shall be interpreted as illustrative and not limiting.

We claim:

1. An immunostimulating composition comprising encapsulating microspheres comprised of (a) a biodegradable-biocompatible poly(DL-lactide-co-glycolideas the bulk matrix produced by a solvent evaporation process wherein the molecular weight of the copolymer is between 4,000 to 100,000 daltons and (b) an immunogenic substance consisting of a conformationally native subunit of chronic intracellular pathogen which, in the course of natural infection with that pathogen, is exposed to the host immune system on the surface of free pathogen and/or pathogen-infected cells.

2. The immunostimulating composition described in claim 1 wherein the antigen is pre-encapsulated into a conformationally stabilizing hydrophilic matrix consisting of an appropriate mono, di- or tri-saccharide or other carbohydrate susbstance by lyophilization prior to its final encapsulation into the PLG microsphere by a solvent extraction process employing acetonitrile as the polymer solvent, mineral oil as the emulsion's external phase, and heptane as the extractant.

3. The immunostimulating compositions described in claims 1 or 2 wherein the immunogenic substance is a native (oligomeric)HIV-1 envelope antigen that is conformationally stabilized by the polymer matrix and serves to elicit in animals the production of HIV specific cytotoxic T lumphocytes and antibodies preferentially reactive against native HIV-1 envelope antigen.

4. The immunostimulating compositions described in claim 3 wherein the amount of said immunogenic substance within the microcapsule comprises between 0.5% to 5.0% of the weight of said composition.

5. The immunostimulating compositions describe in claim 4 wherein the relative ratio between the amount of the lactide:glycolide components of said matrix is within the range of 52:48 to 0:100.

6. The immunostimulating compositions described in claim 5 wherein the molecular weight of said copolymer is between 4,000 to 50,000 daltons.

7. A vaccine consisting of a blend of the immunostimulating compositions described in claims 5 or 6.

8. The immunostimulating compositions described in claim 5, employed as a parentally administered vaccine wherein the diameter size range of said vaccine microspheres lies between 1 nanometer and 20 microns.

9. The immunostimulating compositions described in claim 5, employed as a mucosal vaccine wherein the size of more than 50% (by volume) of said vaccine microspheres is between 5 to 10 microns in diameter.

10. A composition in accordance with claim 1 wherein the microspheres further contain a pharmaceutically-acceptable adjuvant.

11. A vaccine consisting of a blend of the immunostimulating compositions described in claims 5 or 6.

12. The immunostimulating compositions described in claim 6 employed as a parentally administered vaccine wherein the diameter size range of said vaccine microspheres lies between 1 nanometer and 20 microns.

13. The immunostimulating compositions described in claim 7 employed as a parentally administered vaccine wherein the diameter size range of said vaccine microspheres lies between 1 nanometer and 20 microns.

14. The immunostimulating compositions described in claim 6 employed as a mucosal vaccine wherein the size of more than 50% (by volume) of said vaccine microspheres is between 5 to 10 microns in diameter.

* * * * *